(12) United States Patent
Melot et al.

(10) Patent No.: US 6,293,797 B1
(45) Date of Patent: Sep. 25, 2001

(54) PROCESS FOR PRODUCING ARTIFICIAL TEETH IMITATING NATURAL TEETH AND SO-OBTAINED TEETH

(75) Inventors: Charles Melot, Gembloux; Jean-Philippe Lepage, Jambes, both of (BE)

(73) Assignee: Simonis Plastics S.A., Ans (BE)

( * ) Notice: Subject to any disclaimer, the term of this patent is extended or adjusted under 35 U.S.C. 154(b) by 0 days.

(21) Appl. No.: 09/547,651

(22) Filed: Apr. 12, 2000

(51) Int. Cl.[7] ........................................... A61C 13/08
(52) U.S. Cl. ........................................ 433/202.1; 433/223
(58) Field of Search ....................................... 433/213, 214, 433/25, 218, 219, 202.1, 223

(56) References Cited

U.S. PATENT DOCUMENTS 5,773,794   6/1998   Zimet-Sternberg et al. .

FOREIGN PATENT DOCUMENTS

| 2723240 | 7/1994 | (FR) . |
| 05241498 | 9/1993 | (JP) . |
| 11085009 | 3/1999 | (JP) . |
| WO 97/34278 | 9/1997 | (WO) . |

*Primary Examiner*—Nicholas D. Lucchesi
(74) *Attorney, Agent, or Firm*—Knobbe, Martens, Olson & Bear, LLP

(57) ABSTRACT

The present invention relates to a process for producing artificial teeth (1) imitating natural teeth, each tooth comprising a crown (4) and a radicular element (5) comprising one, two or three roots (3), each of said roots comprising at least one radicular canal (7), said process comprising the steps consisting in:

providing a crown (4) by injection into a mould of a plastics having high mechanical strength and hardness properties, providing the radicular element (5) as at least two radicular parts (5A, 5B; 5C, 5D) having a junction surface including at least a slot for providing a radicular canal (7), assembling and joining together the different radicular parts mutually so as to obtain the radicular element (5) of the tooth, and assembling and joining together the crown (4) with said radicular element (5).

12 Claims, 4 Drawing Sheets

PROCESS FOR PRODUCING ARTIFICIAL TEETH IMITATING NATURAL TEETH AND SO-OBTAINED TEETH

This application claims priority under 35 U.S.C. §119(a) to Belgian application BE 09900248, filed Apr. 12, 1999.

OBJECT OF THE INVENTION

The present invention relates to a process for producing artificial teeth imitating natural teeth. Such artificial teeth may be, like natural teeth, one-, two- or three-rooted teeth.

The invention also relates to the products being obtained through said process.

1. Technological Background

To improve training for future dentists, for learning dentistry techniques, in the past jaws provided with their natural teeth were used which were taken particularly from corpses.

For obvious reasons of hygiene, it has been proposed to work on jaws comprising artificial teeth imitating natural teeth the best possible.

An additional use of artificial teeth is to test or demonstrate new care techniques and/or new dental treatment or hygiene devices.

It is known to produce only one artificial crown so as to allow already the practitioners to complete the most current manipulations such as burring, stopping, scaling, etc.

The absence of complete teeth with roots does not allow for a simulation of orthodontics care and proethesis positioning in clinically encountered situations.

2. Prior Art

FR-A-09409450 proposes to produce tooth copies with transparent epoxy resin so as to imitate internal and external tooth anatomies. Such artificial teeth are manufactured by moulding a radicular part upon positioning one or many metal tapering uprights in a mould. The coronary part is made separately also by moulding.

After release and removal of the one or many uprights, those two parts, respectively radicular and coronary, are associated together.

The use of one or many metal supports to be removed to provide canals involves that these must be rectilinear or tapered.

Thus, it is not feasible with said technique to propose bent canals or with a diameter which narrows down and then enlarges as going down to the root tip.

Moreover, it is quite difficult to suit this process to an industrial scale production for said artificial teeth.

Aims of the Invention

The present invention aims to propose a process for producing artificial teeth having a configuration quite close to natural teeth for each type of tooth (incisor, canine, premolar and molar).

The present invention also aims to propose a process for producing artificial teeth by using ; materials the characteristics of which give properties very close to natural tooth components.

The present invention also aims at proposing artificial teeth having shapes and sizes, internal as well as external, which reproduce as much as possible the anatomy of a natural tooth.

The present invention aims more particularly to propose the production of such artificial teeth that have radicular canals the shape of which does not need to be rectilinear, but may be bent and the diameter of which may change as going down within the tooth.

Main Characteristic Elements of the Invention

The present invention relates to a process for producing artificial teeth imitating natural teeth, each tooth comprising a crown and a radicular element comprising one, two or three roots, each of said roots comprising at least one radicular canal, said process comprising the steps consisting in providing a crown by injection into a mould of a plastics having high mechanical strength and hardness properties, providing the radicular element as at least two radicular parts having a junction surface including at least a slot for providing a radicular canal, said production of the different radicular parts being carried out by injection of a material, preferably a material having light s transparency or translucence properties, assembling and joining together the different radicular parts mutually so as to obtain the radicular element of the tooth, and assembling and joining together the crown with said radicular element.

The junction surface is preferably a junction plane provided with the slot(s) that, upon assembling, form a radicular canal, but a junction surface different from a plane may be also provided.

The joining together of the different radicular parts is carried out either by welding through ultrasonic irradiation or by welding through laser ray irradiation.

Moreover it may be provided along the slot(s) provided to create the canal(s) on one of the radicular parts, a material in excess forming an energy leader and on the other radicular part a groove so as to favour the welding of the different radicular parts upon assembling.

Advantageously, joining together the crown and the radicular element is carried out through gluing possibly associated with a polymerization through a UV irradiation.

The present invention also relates to an artificial tooth imitating a natural tooth comprising a crown formed with a material having high hardness and strength properties and a radicular element, preferably light transparent or translucent, consisting in at least two radicular parts joined together along a junction surface including at least a radicular canal Advantageously, the crown of such an artificial tooth is formed with a material reinforced with glass fibres and/or mineral elements, of polyphenylene-sulfone (PPS) or polyarylamide (PAA) type, preferably filled, and the radicular element is formed with a transparent or translucent methyl polymethacrylate (PMMA) or polycarbonate type material.

DESCRIPTION OF A PREFERRED EMBODIMENT OF THE INVENTION

Figure 1:
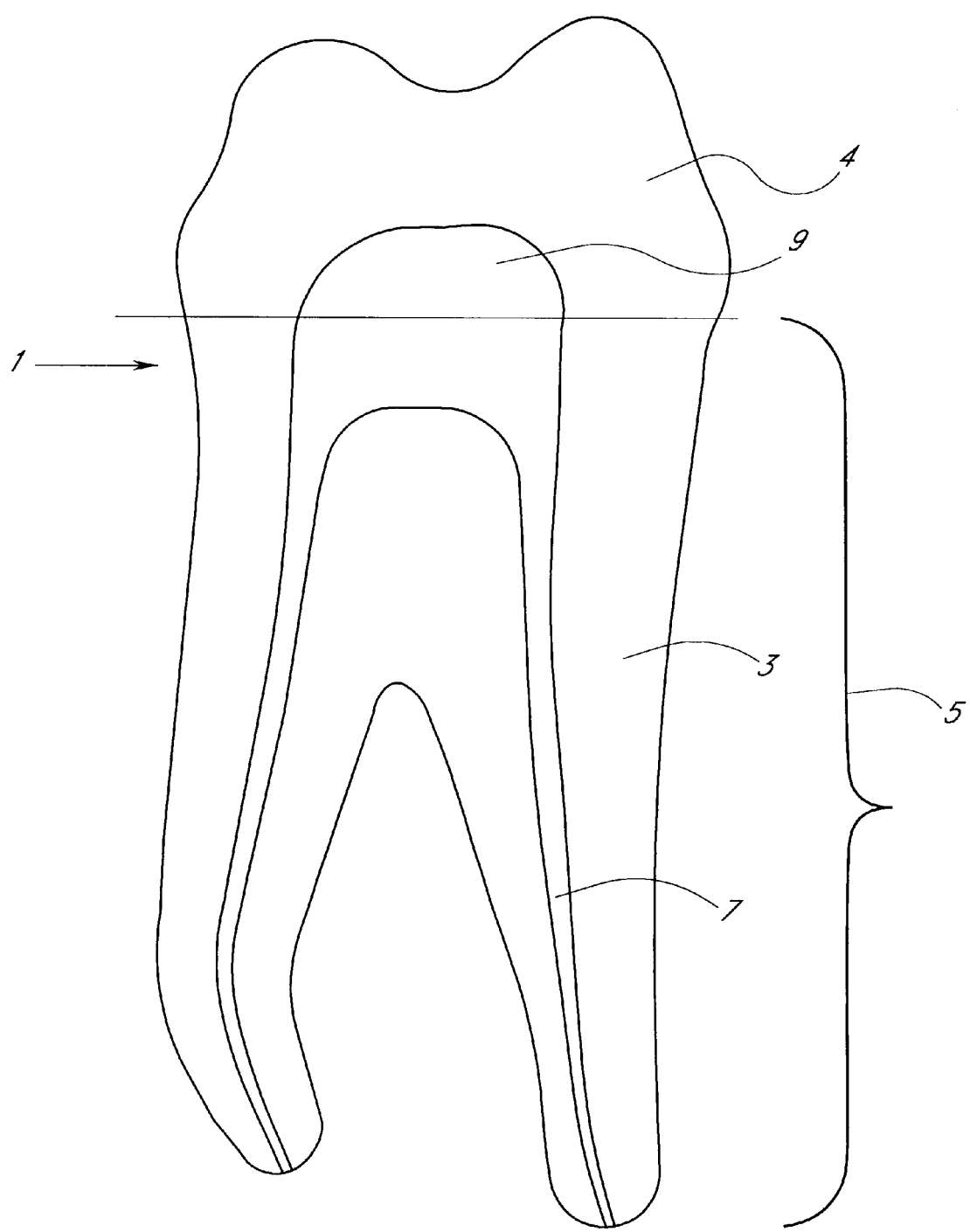
FIG. 1 is a cross section view of a two-rooted half-tooth to be formed with the process according to the present invention.

FIG. 1 is a cross-section view of an half-tooth bearing the general annotation 1 that is to be produced with the process according to the present invention. Such half-tooth 1 comprises essentially two different components. The first one is the crown 4 formed with a material having high mechanical strength and hardness. The second component is the radicular element 5 comprising in the embodiment of FIG. 1 two roots 3 and formed with a transparent material so as to allow to visualize the work being done upon medical care carried out on said teeth.

In each of the roots 3 of the radicular element a radicular canal 7 joined to a pulp cavity 9 is provided. The canal sizes are equivalent to those existing in the reality, namely diameters of about 50 to 150 µm at the apex.

The artificial tooth according to the invention is advantageously formed with materials the minimum mechanical properties of which must meet the following requirements so that the conditions met in the reality are respected workability of the crown 4 with a burr rotating at 120 000 revolutions per minute, workability of the radicular canals 7 manually or with a mechanical burr rotating at 300 revolutions per minute, possibility of stopping the burred radicular canals 7 with a binder the temperature of which may reach 850° C. and which is applied by sputtering through a tool rotating at 5000 revolutions per minute.

Moreover, the tooth 1 must have a sufficient mechanical strength so as to be able to withstand the boring, threading and screwing of a metal pivot for an orthodontics arrangement.

Furthermore, it is required that the shapes and sizes, internal as well as external, of the artificial teeth are as close as possible to an actual anatomy of natural teeth. That should be true for any type of teeth (incisors, canines, premolars and molars) and for any type of canal anatomy.

According to the invention, it is proposed to carry out a process for making different components so as to be able to produce said artificial tooth by moulding plastics by injection. Assembling the crown 4 together with the radicular element 5 is advantageously carried out by ultrasonic welding 15 and/or gluing with UV polymerization.

Figure 2:
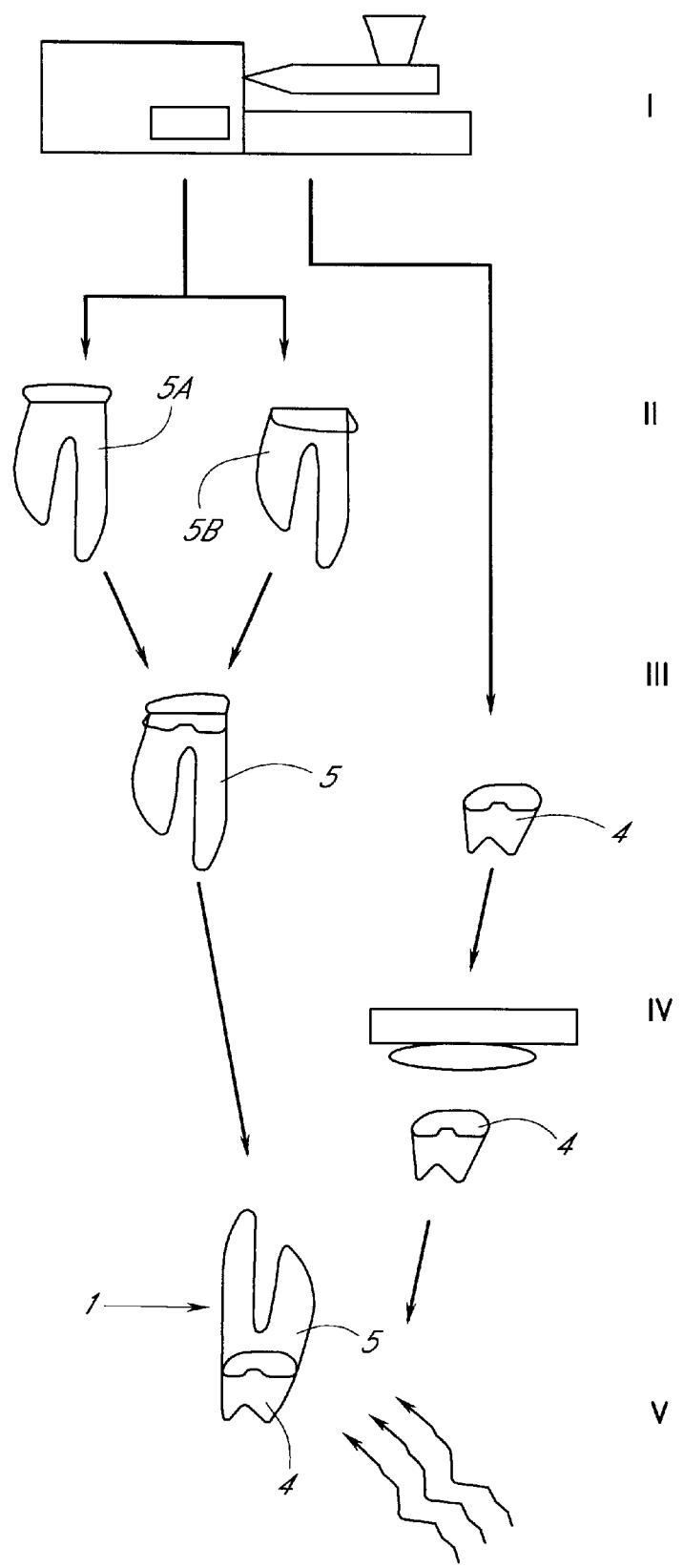
FIG. 2 illustrates an example of a diagram of the various steps implemented to carry out the process according to the present invention.

FIG. 2 is a flow sheet of the various steps implemented to carry out the process according to the invention.

The first step consists in making a mould or a mould part allowing to produce, by injection of different plastics in adequate moulds, the crown 4 and the radicular element 5.

Another technique consists in making at least the radicular element by first moulding a first component (the root itself) provided with a slot and by placing into said slot a second component in the form of a cord imitating the nerve, simultaneously by the bi-injection technique.

Thereafter, the radicular half-parts are joined together in a classical way by superposition.

In the case of the making of a one-rooted tooth 1 (incisor or canine) or a two-rooted tooth (premolar), two radicular parts 5A, 5B are made that will be joined together subsequently according to a junction surface (see step II).

These two radicular parts 5A, 5B are joined together by welding through ultrasonic irradiation (see step III), whereas the crown 4 is glued and positioned precisely onto the assembled root (see step IV).

The two components of the tooth 1 (crown 4+radicular element 5) are maintained into contact for a time period to allow said adhesive to be polymerised, for example through laser ray irradiation (see step V).

According to one of the major characteristics of the present invention, the (bent or plane) junction surface comprises slots that form, upon assembling both radicular parts 5A, 5B, a canal similar to the radicular canal 7 of FIG. 1.

In the particular case of a two-rooted tooth, it may be envisaged particularly advantageously to make a junction surface between the two radicular parts 5A, 5B in the form of a surface plane comprising radicular canals to be made, In more complex cases, in particular in the case where the canals are not located in the same plane or in the case of a three-rooted tooth, such as a molar, it is necessary to envisage to provide one or more junction surfaces where the slots provided to form the radicular canal are located.

Figure 3:
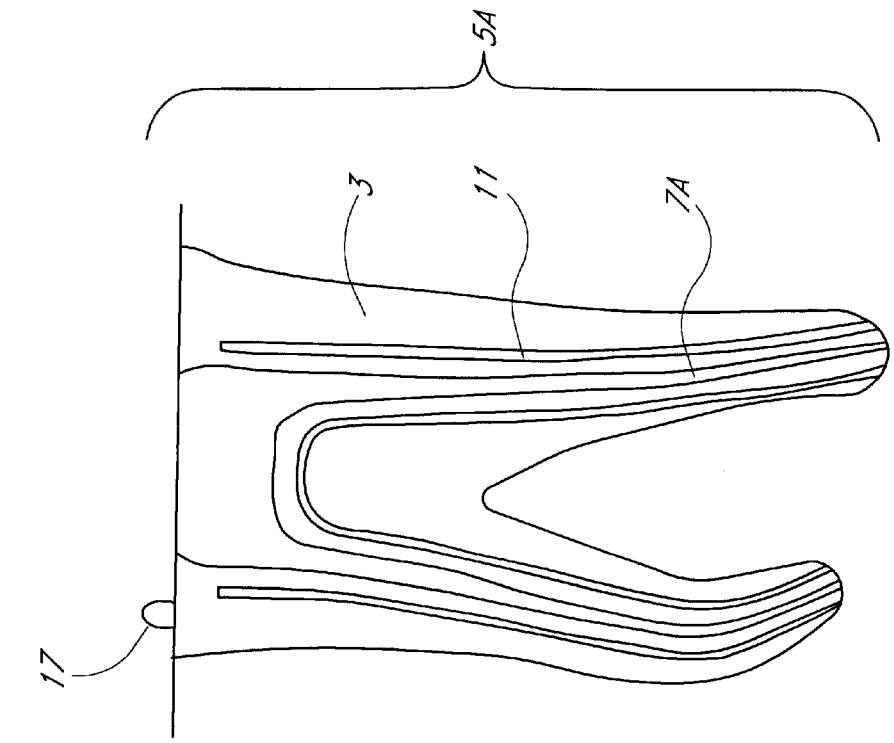
FIG. 3 represents the different components for providing a two-rooted tooth.
Figure 3:
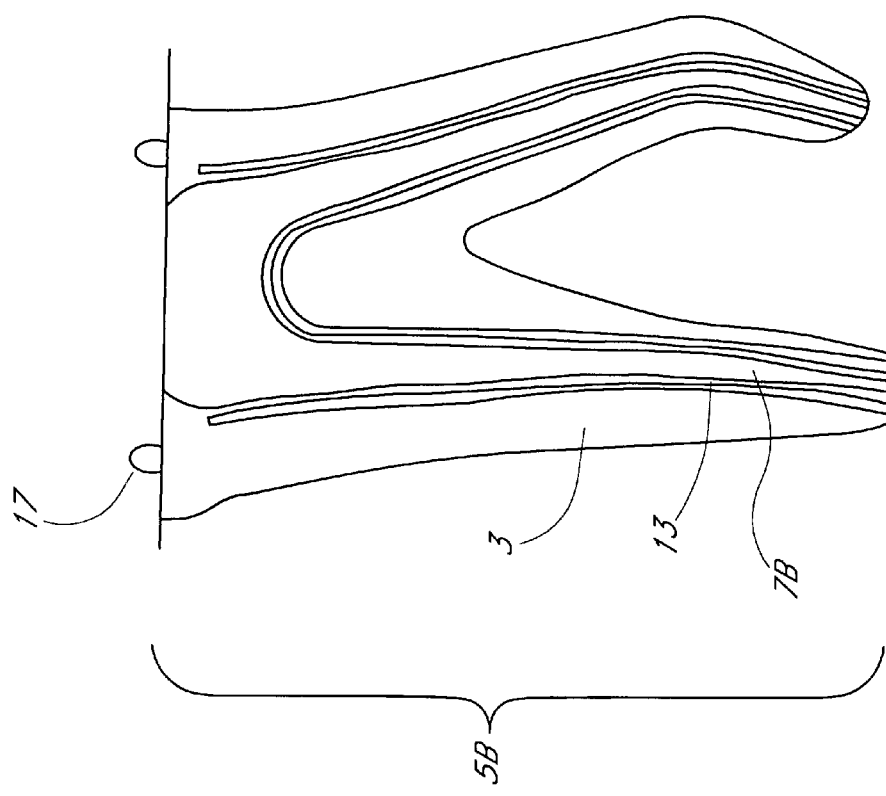

Moreover, in order to promote joining together radicular parts of the radicular element 5, it is provided on at least one of the radicular parts as material in excess 11 located along the slot and on either side of this slot, as illustrated in FIG. 3.

In the corresponding radicular part 3B that must be faced toward said material in excess (not represented in FIG. 1), a groove 13 is provided which allows to accommodate the material in excess 11. Such material in excess 11 acts like an energy leader and makes an efficient joining together easier upon assembling both component radicular parts of the radicular element 5.

Such a technique also allows to reach an improved tightness of the canal being formed and increases naturally the mechanical strength so as to allow the assembling of a mechanical pivot without bursting.

Moreover, it is to be checked upon assembling that the canals are tight so as to be able after working thereupon to inject liquid and possibly quite warm products adapted for example for stopping and treatment of said canals. At that time, a checking of the mechanical strength and aspect of the canals is carried out.

To favour further the location of said radicular element 5 assembled on the crown 4, small teats 17 may be provided on the radicular parts, these teats entering notches 19 provided therefor in the crown.

Working and making roots in various radicular parts allow particularly advantageously to settle the issue of making radicular canals having bends that would prevent an integral moulding in the case of a two-rooted tooth, it is to be observed that such bends are essentially present in a plane that allows to make two half-roots and to assemble them easily by ultrasounds according to a surface corresponding to the junction plane.

Figure 4:
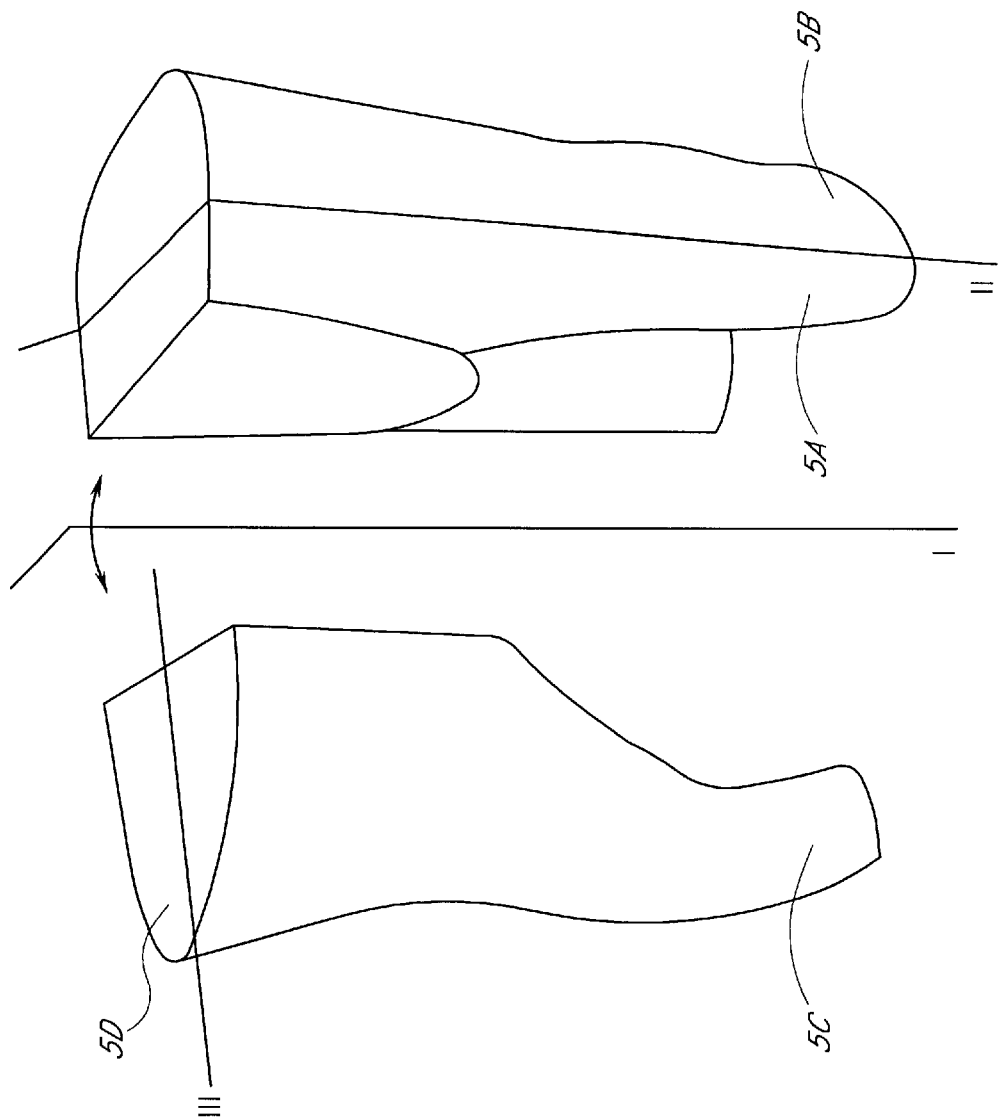
FIG. 4 represents two radicular parts forming the radicular element and intended to be joined together for providing a three-rooted tooth.

In the case of a three-rooted tooth (molars) as illustrated in FIG. 4, a first and a second radicular parts 5A and 5B are firstly made which, upon assembling, allow to create two roots, the radicular canals of which are essentially positioned in the junction plane II.

However, the third root is obtained by assembling a third and a fourth radicular parts 5C and 5D along a junction plane III comprising also the radicular canal corresponding to said root. Thereafter, the first and the second roots are assembled with the third root according to a junction plane I possibly parallel to the junction plane II for forming the three-roots radicular element.

The present invention also aims to propose a solution that allows not only to make main radicular canals existing in true teeth, but also to make secondary radicular canals or branches of smaller sizes also present in true teeth.

What is claimed is:

1. A process for producing artificial teeth imitating natural teeth, each tooth comprising a crown and a radicular element comprising one, two or three roots, each of said roots comprising at least one radicular canal, said process comprising:

providing a crown by injection into a mould of a plastics having high mechanical strength and hardness properties, providing the radicular element as at least two radicular parts having a junction surface including at least a slot for providing a radicular canal, assembling and joining together the different radicular parts mutually so as to obtain the radicular element of the tooth, and assembling and joining together the crown with said radicular element.

2. The process according to claim 1, wherein said radicular element is formed with a material having light transparency or translucence properties.

3. The process according to claim 1 wherein the junction surface of the radicular parts comprises a junction plane provided with slots that, upon assembling the radicular parts, form one or more canals.

4. The process according to claim 1 wherein said joining together the various radicular parts is carried out either by welding through ultrasonic irradiation or by welding through laser ray irradiation.

5. The process according to claim 1 wherein there is provided along the slot(s) provided to create the canal(s) on one of the radicular parts, a material in excess forming an energy leader and on the other radicular part a groove so as to favor the welding of the different radicular parts upon assembling.

6. The process according to claim 1 wherein said joining together the crown and the radicular element is carried out through gluing.

7. The process of claim 6 wherein said gluing is associated with a polymerization through a UV irradiation.

8. An artificial tooth imitating a natural tooth comprising a crown formed with a material having high hardness and strength properties and a radicular element comprising at least two radicular parts joined together along a junction surface including at least a radicular canal.

9. The artificial tooth according to claim 8, wherein the radicular element is formed with a light transparent or translucent material.

10. The artificial tooth according to claim 9, wherein the radicular element is formed with a transparent or translucent material of methyl methacrylate (PMMA) or polycarbonate type.

11. The artificial tooth according to claim 8, wherein the crown is formed with a material reinforced with glass fibers and/or mineral elements of polyphenylene-sulfone (PPS) or polyarylamide (PAA) type.

12. The artificial tooth according to claim 11 wherein the crown glass fibers and/or mineral elements of polyphenylene-sulfone (PPS) or polyarylamaide (PAA) type are filled.

* * * * *